United States Patent
Kang

(10) Patent No.: US 8,877,736 B2
(45) Date of Patent: Nov. 4, 2014

(54) METHOD FOR TREATING KELOID BY ADMINISTERING 3'SIALYLLACTOSE OR 6'SIALYLLACTOSE AS A PHARMACEUTICAL OR COSMETIC

(75) Inventor: Seung Woo Kang, Seoul (KR)

(73) Assignee: Benebiosis Co., Ltd., Seoul (KR)

( * ) Notice: Subject to any disclaimer, the term of this patent is extended or adjusted under 35 U.S.C. 154(b) by 0 days.

(21) Appl. No.: 13/376,463

(22) PCT Filed: Apr. 9, 2010

(86) PCT No.: PCT/KR2010/002210
§ 371 (c)(1),
(2), (4) Date: Jan. 3, 2012

(87) PCT Pub. No.: WO2010/117241
PCT Pub. Date: Oct. 14, 2010

(65) Prior Publication Data
US 2012/0122814 A1 May 17, 2012

(30) Foreign Application Priority Data
Apr. 9, 2009 (KR) .................. 10-2009-0030995

(51) Int. Cl.
| | | |
|---|---|---|
| A61K 31/702 | (2006.01) | |
| A61P 17/02 | (2006.01) | |
| C07D 257/04 | (2006.01) | |
| A61K 31/7016 | (2006.01) | |
| A61K 8/60 | (2006.01) | |

(52) U.S. Cl.
CPC ............ A61K 31/702 (2013.01); C07D 257/04 (2013.01); A61K 31/7016 (2013.01); A61K 8/60 (2013.01)
USPC .......................................................... 514/54

(58) Field of Classification Search
CPC ..... A61K 8/00; A61K 31/7016; A61K 31/70; A61K 31/702; C13K 5/00; C13K 13/00; C07H 3/00
See application file for complete search history.

(56) References Cited

U.S. PATENT DOCUMENTS 6,008,203 A * 12/1999 Magnani et al. ............... 514/61
6,576,251 B1   6/2003 Stahl et al.

FOREIGN PATENT DOCUMENTS

WO    WO 9848817 A1 * 11/1998 ............ A61K 31/715

OTHER PUBLICATIONS

Al-Attar, Ali, et al. "Keloid pathogenesis and treatment." Plastic and reconstructive surgery 117.1 (2006): 286-300.*
Mussatto, Solange I., and Ismael M. Mancilha. "Non-digestible oligosaccharides: A review." Carbohydrate polymers 68.3 (2007): 587-597.*
"Prevention" in Glossary of medical education terms: Parts 1-7. Wojtczak, A., Ed. Medical Teacher. vol. 24, Nos. 2-6 and vol. 25, No. 1&2. 2002.*
van der Veer, W. M., Bloemen, M. C., Ulrich, M. M., Molema, G., van Zuijlen, P. P., Middelkoop, E., & Niessen, F. B. (2009). Potential cellular and molecular causes of hypertrophic scar formation. Burns, 35(1), 15-29.*
Beer, T. W., Baldwin, H. C., Goddard, J. R., Gallagher, P. J., & Wright, D. H. (1998). Angiogenesis in pathological and surgical scars. Human pathology, 29(11), 1273-1278.*
Al-Attar, A., Mess, S., Thomassen, J. M., Kauffman, C. L., & Davison, S. P. (2006). Keloid pathogenesis and treatment. Plastic and reconstructive surgery, 117(1), 286-300.*
Daddaoua et al. "Goat Milk Oligosaccharides are Anti-Inflammatory in Rats with Hapten-Induced Colitis," J. Nutr. 136:672-676, 2006.
International Search Report from PCT/KR2010/002210 dated Jan. 31, 2011 (date of completion of search) and Feb. 1, 2011 (date of mailing of report).

* cited by examiner

Primary Examiner — Shaojia Anna Jiang
Assistant Examiner — Dale R Miller
(74) Attorney, Agent, or Firm — Clark & Elbing LLP

(57) ABSTRACT

The present invention relates to a composition for preventing or treating hypertrophic scar or keloid, comprising as an active ingredient a compound represented by the following general formula I:

$$S\text{-}(MS)_p\text{-}(MS)_q \qquad (I)$$

Figure 1:
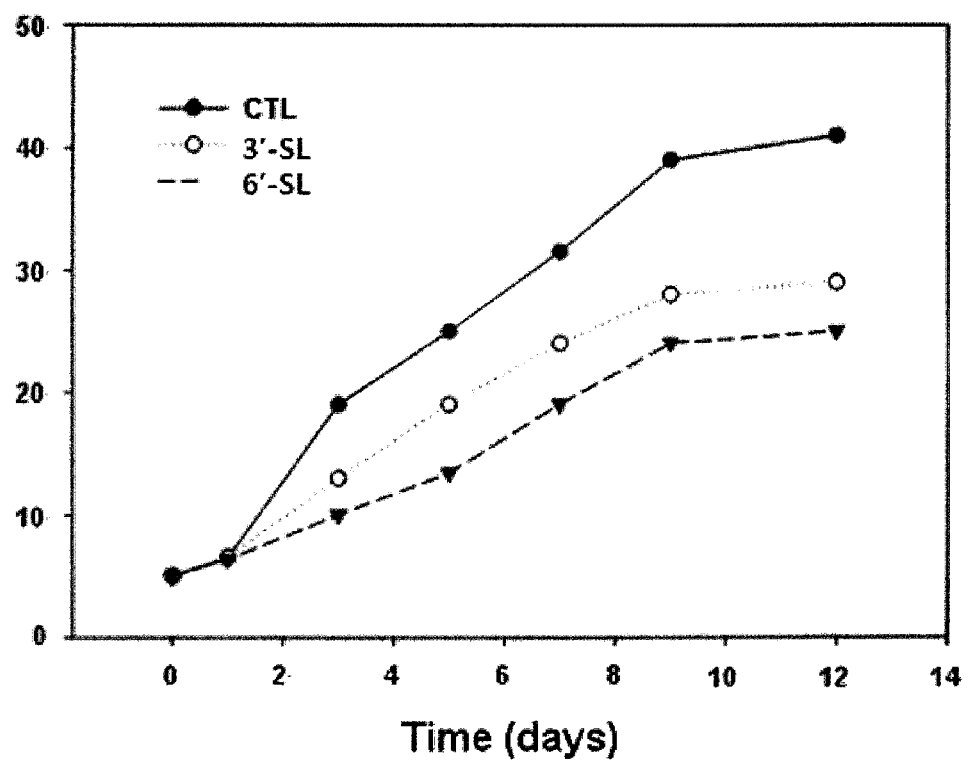

wherein S represents sialic acid, and $(MS)_p$ and $(MS)_q$ independently represent a monosaccharide residue.

The composition of the present invention inhibits proliferation of keloid fibroblasts and induces apoptosis of keloid fibroblasts, thereby effectively preventing or treating keloid. The active ingredient used in this invention is a natural compound or its derivative or isomer and therefore very safe to human.

6 Claims, 5 Drawing Sheets

METHOD FOR TREATING KELOID BY ADMINISTERING 3'SIALYLLACTOSE OR 6'SIALYLLACTOSE AS A PHARMACEUTICAL OR COSMETIC

CROSS-REFERENCE TO RELATED APPLICATIONS

This application is the U.S. national stage filing under 35 U.S.C. §371 of international application PCT/KR2010/00221, filed Apr. 9, 2010, which claims benefit of Korean Patent Application 10-2009-0030995, Apr. 9, 2009.

TECHNICAL FIELD

The present invention relates to compositions for preventing or treating hypertrophic scar or keloid.

BACKGROUND ART

Keloid is a type of hypertrophic scars. It is characterized by abnormal proliferation of tissues found within scar tissue that is caused by skin adhesion after artificial damages such as burns, surgical wounds, piercings and tattoo. Keloid sometimes occurs spontaneously. Infection into keloids may cause ulcer. To date, removing scars completely is considered as a sole therapy. In general, probability that a surgery scar becomes keloid is as high as 50%.

Keloid is formed within scar tissues and characterized by fibroblastoma as benign tumors. It tends to overgrow larger than size of original scars.

Currently, while several surgical therapies have been suggested, there is no way to treat keloid with 100% probability. However, all surgical methods to remove scars have high recurrence of keloids. To make matters worse, overgrown keloids may be caused after surgical operations.

There are other treatment approaches for keloids as follows:

Contractubex gel/Hexilak gel has been used to treat keloids. These gels include onion extract, heparin and allantoin. These gels firstly developed for the treatment of scar after thyroidectomy are being currently prescribed for treatment of wounds of all trauma (burns, acne and piercings), post-operative wounds or keloids. While this therapeutic approach is simple, it requires patience of patients.

The mucus of Helix aspersa Muller snail has been used for treatment of keloids. The topical application of this mucus to keloids results in reduced proliferation of hypodermis fibroblast and suppression of excessive collagen production, inhibiting or reducing keloids and hypertrophic scars.

A humidity dressing of silicone gel has been employed for suppression of keloids. This treatment is safe and painless but it has serious problem of severe itching associated with prolonged application.

In addition, a steroid injection is being used for treatment of keloids. The injection of triamcinolone acetonide or other corticosteroids may reduce keloid size and irritation. However, this therapy needs anesthesia for large-sized keloids.

Besides, several therapies such as crimp band, frozen surgical techniques, radiation therapy and laser treatments are being used for the treatment of keloids. Ethanol amine (U.S. Pat. No. 5,128,375) and CM101/GBS toxin (U.S. Pat. No. 6,569,838) are proposed for the treatment of keloids.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The inventors of the present invention have made efforts to develop a substance capable of preventing or treating preventing or treating hypertrophic scar or keloid and having no or little adverse effects. As a result, they have discovered that sialyloligosaccharide inhibits proliferation of keloid fibroblasts and induces apoptosis of keloid fibroblasts, thereby preventing or treating preventing or treating hypertrophic scar or keloid.

Accordingly, it is an object of this invention to provide a composition for preventing or treating hypertrophic scar or keloid.

It is another object of this invention to provide a method for preventing or treating hypertrophic scar or keloid.

Other objects and advantages of the present invention will become apparent from the detailed description to follow taken in conjugation with the appended claims and drawings.

In one aspect of this invention, there is provided a composition for preventing or treating hypertrophic scar or keloid, comprising as an active ingredient a compound represented by the following general formula I:

$$\text{S-(MS)}_p\text{-(MS)}_q \qquad (I)$$

wherein S represents sialic acid, and $(MS)_p$ and $(MS)_q$ independently represent a monosaccharide residue.

In another aspect of this invention, there is provided a method for preventing or treating hypertrophic scar or keloid, comprising administering to a subject a composition comprising as an active ingredient a compound represented by the following general formula I:

$$\text{S-(MS)}_p\text{-(MS)}_q \qquad (I)$$

wherein S represents sialic acid, and $(MS)_p$ and $(MS)_q$ independently represent a monosaccharide residue.

The inventors of the present invention have made efforts to develop a substance capable of preventing or treating preventing or treating hypertrophic scar or keloid and having no or little adverse effects. As a result, they have discovered that sialyloligosaccharide inhibits proliferation of keloid fibroblasts and induces apoptosis of keloid fibroblasts, thereby preventing or treating preventing or treating hypertrophic scar or keloid.

In the present invention, the active ingredient is a compound represented by General Formula I. In General Formula I, S represents sialic acid. Sialic acid may be bound to MSp in various manners. It may be bound to the monosaccharide compound (MS)p via α-2,3 or α-2,6 linkage. In addition to sialic acid, S may be modified sialic acid. For example, S may be sialic acid with the —OH group at the C4-position modified (e.g. by $C_1$-$C_4$ alkyl). Most preferably, S is unmodified sialic acid.

The monosaccharide compounds (MS)p and (MS)q may be any monosaccharide compound known in the art. For example, tetroses (e.g., erythrose and threose), pentoses (e.g., ribose, arabinose, xylose and lyxose) and hexoses (allose, altrose, glucose, mannose, gulose, idose, galactose and talose) are included. The monosaccharide compounds (MS)p and (MS)q may be preferably a pentose or a hexose, more preferably a hexose, further more preferably, glucose, mannose or galactose, and most preferably, glucose or galactose. The monosaccharide compounds (MS)p and (MS)q may be a D- or L-stereoisomer, most preferably a D-stereoisomer.

(MS)p and (MS)q may be the same or different monosaccharide compound. Preferably, they are different monosaccharide compounds.

According to a preferred embodiment of the present invention, (MS)p is galactose or glucose, and (MS)q is glucose or galactose. Most preferably, (MS)p is galactose and (MS)q is glucose. When (MS)p is galactose and (MS)q is glucose, the disaccharide compound lactose is obtained.

The monosaccharide compounds (MS)p and (MS)q may be modified or unmodified. For example, a monosaccharide compound with the -OH group bound to acetyl or N-acetyl may be used. Preferably, the monosaccharide compounds (MS)p and (MS)q are unmodified monosaccharide compounds.

The most preferred embodiment of the compound represented by General Formula I, which is used as the effective ingredient in the present invention, is sialyllactose. Sialyllactose, which is used as the effective ingredient in the present invention, is a compound formed by sequentially bound sialic acid, galactose and glucose.

Sialic acid may be bound to galactose in various manners, e.g. via $\alpha$-2,3 or $\alpha$-2,6 linkage. Sialic acid may be modified. For example, the —OH group at the C4-position of sialic acid may be modified (e.g. by $C_1$-$C_4$ alkyl).

The galactose and glucose in the sialyllactose may be D- or L-stereoisomers, most preferably D-stereoisomers. The galactose and glucose may be modified or unmodified. For example, the —OH group of the monosaccharide compound may be bound to acetyl or N-acetyl. Preferably, the galactose and glucose in the sialyllactose are unmodified monosaccharides.

According to a preferred embodiment of the present invention, the sialyllactose used in the present invention as the effective ingredient is $\alpha$-NeuNAc-(2→3)-$\beta$-D-Gal-(1→4)-D-Glc or $\alpha$-NeuNAc-(2→6)-$\beta$-D-Gal-(1→44)-D-Glc [NeuNAc: N-acetylneuraminyl, Gal: galactose, Glc: glucose]. $\alpha$-NeuNAc-(2→3)-$\beta$-D-Gal-(1→4)-D-Glc is a substance found in GM3 ganglioside, and $\alpha$-NeuNAc-(2→6)-$\beta$-D-Gal-(1→4)-D-Glc is its isomer.

More preferably, the sialyllactose used in the present invention as the effective ingredient is $\alpha$-NeuNAc-(2→6)-$\beta$-D-Gal-(1→4)-D-Glc. As demonstrated in the examples below, $\alpha$-NeuNAc-(2→6)-$\beta$-D-Gal-(1→4)-D-Glc is superior to $\alpha$-NeuNAc-(2→3)-$\beta$-D-Gal-(1→4)-D-Glc in inhibition of keloid fibroblast proliferation and induction of apoptosis of keloid fibroblast.

In the composition of the present invention, in addition to the above-described compound itself, a pharmaceutically acceptable salt, hydrate or solvate thereof may be used as the effective ingredient.

The term "pharmaceutically acceptable salt" refers to a salt of the compound that produces the desired pharmacological effect, i.e. reduction of body weight and LDL-cholesterol. The salt is formed by using an inorganic acid (e.g., hydrochloride, hydrobromide and hydroiodide) or an organic acid (e.g., acetate, adipate, alginate, aspartate, benzoate, benzenesulfoate, p-toluenesulfoate, bisulfate, sulfamate, sulfate, naphtalate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, 2-hydroxyethanesulfonate, lactate, maleate, methanesulfonate, 2-naphthalenesulfonate, nicotinate, oxalate, tosylate and undecanoate).

The term "pharmaceutically acceptable hydrate" refers to a hydrate of the compound that produces the desired pharmacological effect. The term "pharmaceutically acceptable solvate" refers to a solvate of the compound that produces the desired pharmacological effect. The hydrate and the solvate may also be prepared using the aforementioned acids.

The term used herein "hypertrophic scars" refers to non-proliferative lump that is a red raised lump on the skin, and the term "keloid" refers to a proliferative lump that is one type of hypertrophic scars.

According to a preferred embodiment, the composition of the present invention inhibits proliferation of keloid fibroblasts or induces apoptosis of keloid fibroblasts, thereby exhibiting capability of preventing or treating keloid.

The composition of the present invention may be prepared into a pharmaceutical composition or a functional cosmetic composition.

According to a preferred embodiment of the present invention, the composition of the present invention is a pharmaceutical composition comprising (a) a pharmaceutically effective amount of the compound of the present invention represented by General Formula I; and (b) a pharmaceutically acceptable carrier.

As used herein, the term "pharmaceutically effective amount" refers to an amount sufficient to attain the effect or activity of the compound represented by General Formula I.

When the composition of the present invention is prepared into a pharmaceutical composition, the pharmaceutical composition of the present invention comprises a pharmaceutically acceptable carrier. The pharmaceutically acceptable carrier comprised in the pharmaceutical composition of the present invention is one commonly used in formulations and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present invention may further comprise, in addition to aforesaid ingredients, a lubricant, a wetting agent, a sweetener, a flavor, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present invention may be administered orally or parenterally. In case of parenteral administration, it may be administered through intravenous injection, subcutaneous injection, intramuscular injection, intraperitoneal injection or transdermal administration. Considering the application of the present composition to treatment of hypertrophic scars or keloid, it is preferable that the present composition is administered by topical application to the skin.

An adequate administration amount of the pharmaceutical composition of the present invention may vary depending on various factors including formulation method, administration method, age, weight, sex or disease condition of the patient, diet, administration time, administration route, elimination rate and response sensitivity. The pharmaceutical composition of the present invention may be preferably administered, for an adult, in an amount of 0.001-100 mg/kg (body weight) per day, more preferably 0.01-80 mg/kg (body weight), most preferably 0.1-60 mg/kg (body weight). Also, under the discretion of the physician or pharmacist, it may be administered once or several times per day.

The pharmaceutical of the present invention may be prepared according to a method that may be easily carried out by those skilled in the art in single-dose forms or in multi-dose packages using a pharmaceutically acceptable carrier and/or excipient.

According to a preferred embodiment of the present invention, a formulation of the composition of the present invention may be solution, suspension, syrup, emulsion, liposome, extract, dust, powder, granule, tablet, sustained-release formulation or capsule, and may further comprise a dispersant or a stabilizer.

According to a preferred embodiment, the composition of the present invention is a functional cosmetic composition.

The cosmetic composition of this invention comprises not only the compound represented by the general formula I but also ingredients conventionally used in cosmetic compositions such as auxiliaries including stabilizers, solubilizers, Vitamins, colorants and flavors, and carriers.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances.

The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum metahydroxide, bentonite, agar and tragacanth or mixtures of these substances.

The formulation of soap may comprise alkali metal salts of fatty acids, salts of fatty acid hemiesters, fatty acid protein hydrolyzates, isethionates, lanolin, fatty alcohol, vegetable oil, glycerol, sugars or mixtures of these substances.

The formulation of a surfactant-containing cleanser may comprise as carriers aliphatic alcohol sulfate, aliphatic alcohol ether sulfate, sulfosuccinic acid monoester, isethionate, imidazoliniurn derivatives, methyltaurate, sarcosinate, fatty acid amide ether sulfate, alkylamidobetaine, aliphatic alcohols, fatty acid glycerides, fatty acid diethanolamide, plant oils, lanolin derivatives or ethoxylated glycerol fatty acid ester.

The features and advantages of this invention are summarized as follows:

(a) The composition for preventing or treating hypertrophic scars or keloid comprises as active ingredients siallyoligosaccharides.

(b) The composition of the present invention inhibits proliferation of keloid fibroblasts and induces apoptosis of keloid fibroblasts, thereby effectively preventing or treating keloid.

(c) The active ingredient used in this invention is a natural compound or its derivative or isomer and therefore very safe to human.

BRIEF DESCRIPTIONS OF DRAWINGS

FIG. 1 represents the results of the growth of keloid fibroblasts treated with 3' sialyllactose (3'-SL), 6' sialyllactose (6'-SL) and excipient (CTL: negative control), respectively. Y-axis represents the number of cells. A unit is $1 \times 10^4$.

Figure 2:
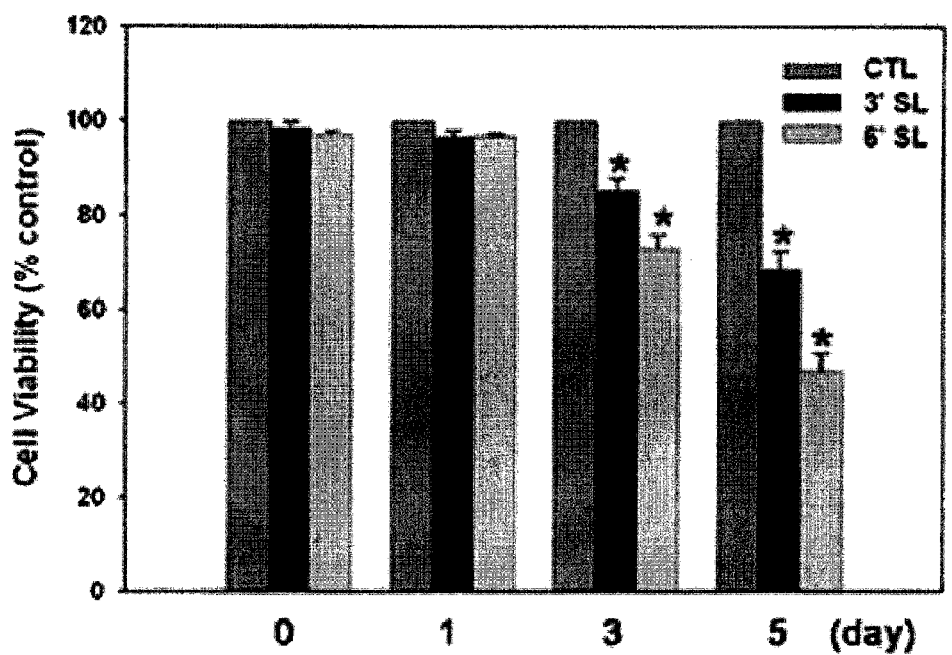

FIG. 2 represents the results of inhibitory effect on the proliferation of keloid fibroblasts treated with sialyllactose. 3'SL and 6'SL represent 3'-sialyllactose and 6'-sialyllactose, respectively. CTL is a negative control.

Figure 3:
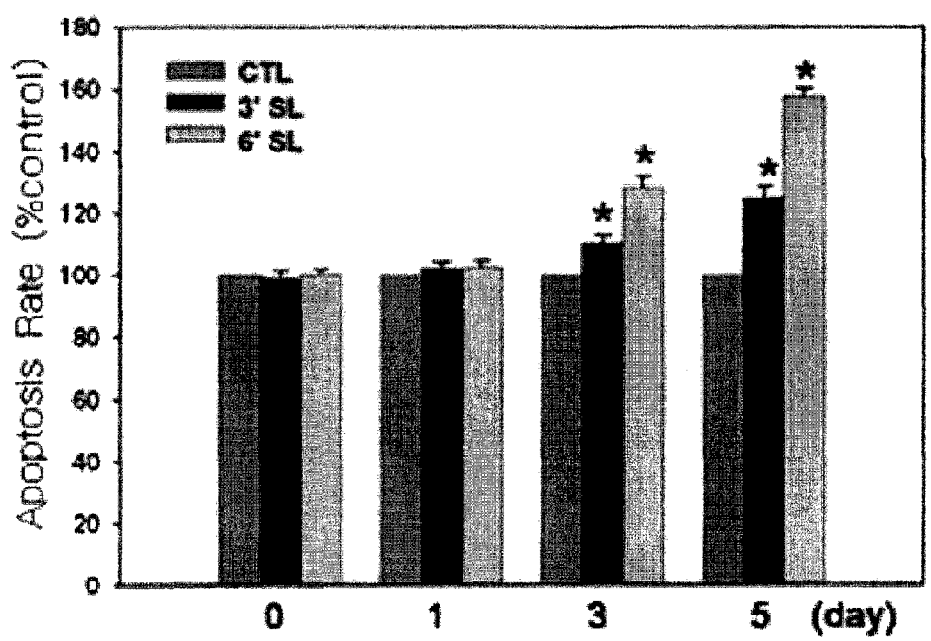

FIG. 3 represents the results of the TUNEL analysis for apoptosis of keloid fibroblasts treated with sialyllactose. 3'SL and 6'SL represent 3'-sialyllactose and 6'-sialyllactose, respectively. CTL is a negative control.

Figure 4A:
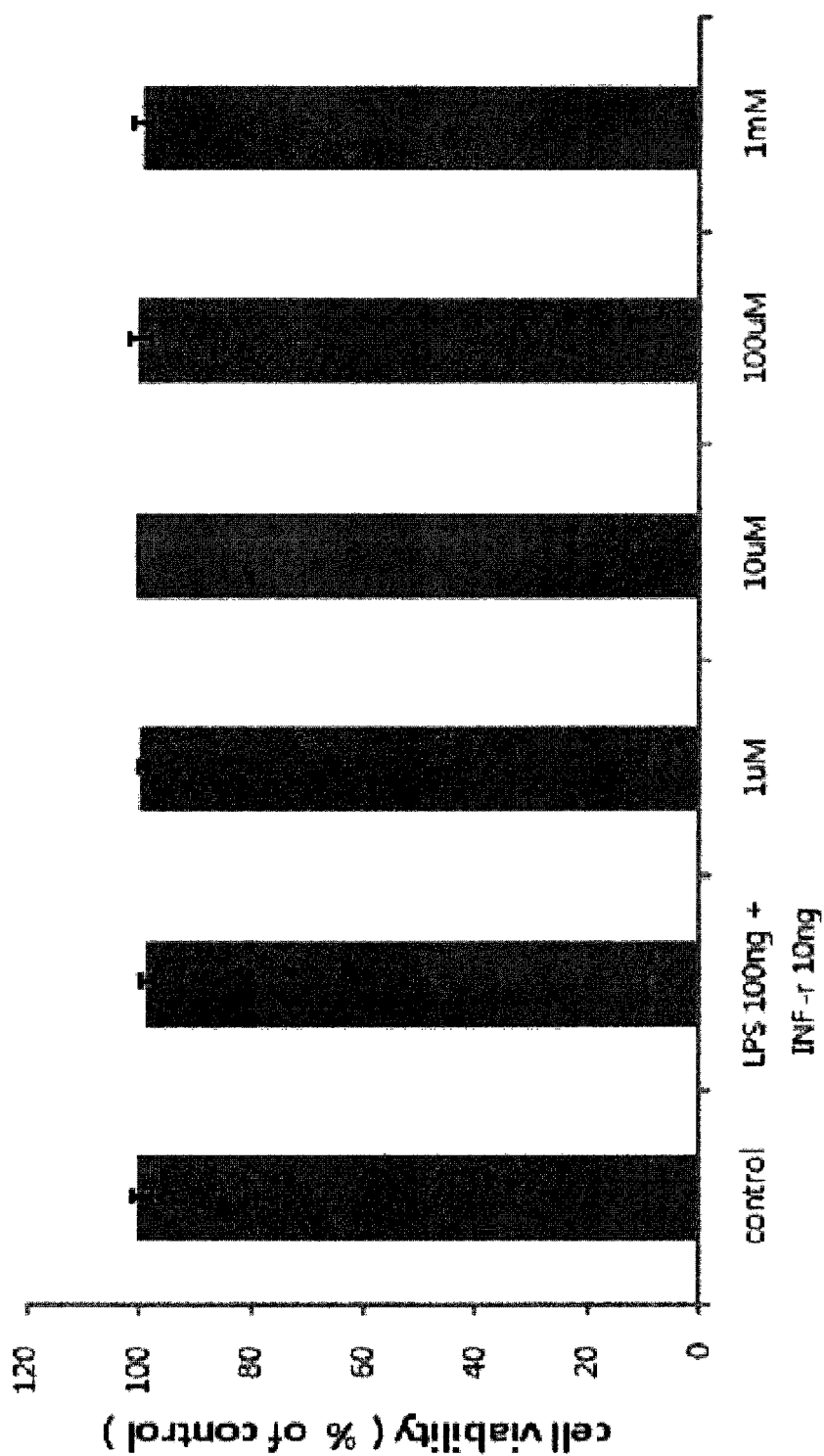
Figure 4B:
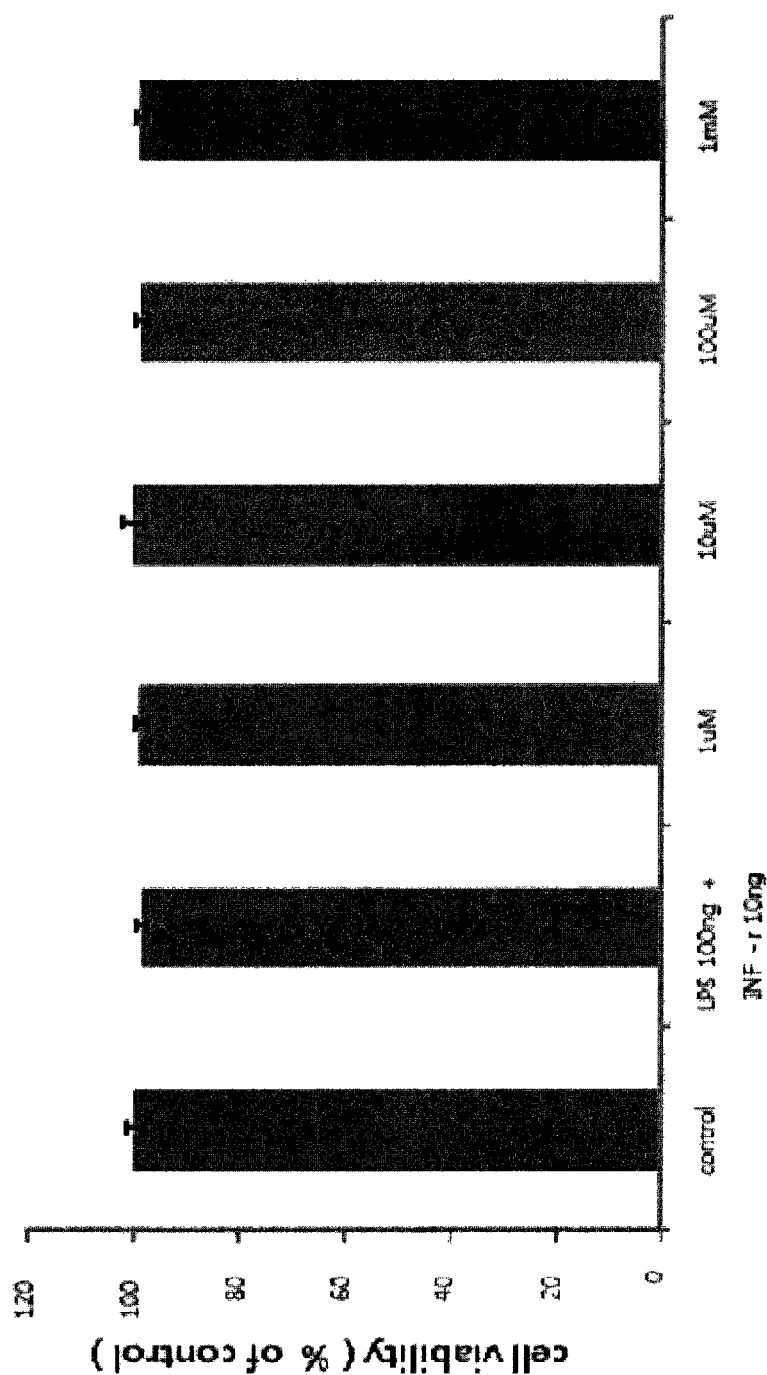

FIG. 4 represents the results of effect on proliferation of RAW 264.7 cells treated with sialyllactose. FIG. 4a corresponds to 3' sialyllactose and FIG. 4b to 6'-sialyllactose. CTL is a negative control.

The present invention will now be described in further detail by examples. It would be obvious to those skilled in the art that these examples are intended to be more concretely illustrative and the scope of the present invention as set forth in the appended claims is not limited to or by the examples.

EXAMPLES

Material and Method

Cell Culture of Keloid Fibroblasts

Human keloid fibroblasts (CRL 1762) were purchased from ATCC. Medium has the following composition: DMEM (Dulbecco's Modified Eagle's Medium), 4 mM L-glutamine, 100 μg/ml streptomycin, 100 U/ml penicillin and 10% fetal bovine serum. The fibroblasts were incubated at 37° C. in a $CO_2$ incubator under humid atmosphere (5% $CO_2$, 95% air). Medium was replaced every 3-4 days.

Analysis of Cell Proliferation

1. Cell Counting

Keloid fibroblasts (KF) were plated at $5 \times 10^4$ cells/well in a 6-well plate. 24 hours later, KF was incubated with 1 mM 3'-sialyllactose (3'-SL), 6'-sialyllactose (6'-SL) or excipient (Phosphate buffered saline, PBS). 3'-Sialyllactose (3'-N-Acetylneuraminyl-D-lactose, 3'-Sialyl-D-lactose or α-Neu-NAc-(2→3)-β-D-Gal-(1→4)-D-Glc) or 6'-sialyllactose (6'-N-Acetylneuraminyl-lactose, 6'-Sialyl-D-lactose, or α-NeuNAc-(2→6)-β-D-Gal-(1→4)-D-Glc) were purchased from Sigma-Aldrich. After 0, 1, 5, 7, 9, and 12 days, KF was collected using trypsin-EDTA and stained with trypan blue, followed by cell counting using a blood cell counter (C-Chip DHC N15, Incyto).

2. Analysis of XTT

The rate of cell proliferation was measured using Roche's Cell Proliferation Kit II (XTT) system. Keloid fibroblasts (KF) were plated at $2.0 \times 10^3$ cells/well in a 96-well plate and then treated 3'-SL, 6'-SL and PBS at a concentration of 1 mM, respectively. After 0, 1, 3 and 5 days, KF was incubated with 50 μl/well of XTT (sodium 3'-[1-(phenylaminocarbonyl)-3, 4-tetrazolium]-bis(4-methoxy-6-nitro) benzene sulfonic acid hydrate) reagent for 4 hr at 37° C. and the absorbance at 470 nm was measured using a microplate reader. The relative survival rates of groups treated with sialyllactose were calculated with reference to untreated sialyllactose group (i.e., excipient treatment group, 100% survival rate).

Analysis of Apoptosis (TUNEL)

Using in situ cell death detection kit (TUNEL, Roche Diagnostics), apoptosis was analyzed and DNA fragmentation in keloid fibroblasts was quantified. A single layer of keloid fibroblasts was cultured directly in a tissue culture flask and then incubated with 1 mM 3'-SL, 6'-SL or PBS. Following 0, 1, 3 and 5 days, the analysis was carried out according to the manufacturer's manual.

Analysis of Cytotoxicity

Cytotoxicity of sialyllactose to cells other than keloid fibroblasts was analyzed RAW 264.7 cells (TIB-71) were purchased from ATCC. Dulbecco's Modified Eagle's Medium (DMEM) was purchased from JBI and supplemented with 100 U/ml penicillin, 100 µg/ml streptomycin, and 10% fetal bovine serum (FBS). Medium was replaced every 3-4 days. The cells were incubated at 37° C. in a $CO_2$ incubator. For investigation of cell proliferation rate, MTT quantification was performed. RAW 264.7 cells were plated at $2.0 \times 10^3$ cells/well in a 96-well plate and 3'-SL or 6'-SL was treated at a concentration of 0.001, 0.01, 0.1, and 1 mM. A negative control group was treated with PBS. After 5 days, the cells were incubated with 500 µg/ml MTT solution for 4 hr at 37° C. Five days later, the absorbance at 540 nm was measured using formazan in diumsulfoxide (DMSO). The relative survival rates of groups treated with sialyllactose were calculated with reference to untreated sialyllactose group (i.e., PBS treatment group, 100% survival rate).

Statistic Analysis

The XTT and TUNEL test results were expressed as mean ±standard error. The average values were given by at least three independent experiments. To compare average values between treatment groups, Student's t-test was performed. A p-value less than 0.01 (p<0.01) was considered statistically significant.

Results

SL(sialyllactose) Inhibits Cell Proliferation of Keloid Fibroblasts

To elucidate that SL inhibits the formation of keloids, keloid fibroblasts were treated with SL and incubated for a period of time, followed by cell counting. As shown in FIG. 1, the growth of keloid fibroblasts were considerably inhibited by 3' sialyllactose (3'-SL) and 6' sialyllactose (6'-SL) comparing with a negative control (CTL). Interestingly, the growth of keloid fibroblasts was more significantly inhibited by 6'-SL than the 3'-SL.

In the MTT analysis (FIG. 2), the proliferation of keloid fibroblasts were also considerably inhibited by 3'-SL and 6'-SL comparing with a negative control (CTL). The proliferation of keloid fibroblasts was more significantly inhibited by 6'-SL than the 3'-SL.

SL Induces Apoptosis of Keloid Fibroblasts

To verify that SL induces apoptosis of keloid fibroblasts, the TUNEL analysis was carried out. As represented in FIG. 3, the apoptosis of keloid fibroblasts were induced by either 3' SL or 6' SL. The apoptosis of keloid fibroblasts was more significantly inhibited by 6'-SL than the 3'-SL.

SL(sialyllactose) Did Not Inhibit Cell Proliferation of Non-Keloid Fibroblasts

To test that SL affects cell proliferation of non-keloid fibroblasts, RAW 264.7 cells were incubated with SL for a period of time and the MTT assay were performed. As represented in FIGS. 4a-4b, the proliferation of RAW 264.7 cells was not affected by either 3' SL or 6' SL in comparing with a negative control (CTL), demonstrating that SL dose not inhibit cell proliferation of non-keloid fibroblasts.

Taken together, it would be appreciated that SL inhibits the proliferation of keloid fibroblasts and induces apoptosis effectively. 6'-SL has higher potency than 3'-SL. In addition, SL does not affect cell proliferation of non-keloid fibroblasts. Consequently, it would be concluded that SL can prevent or treat keloids.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for treating keloid, comprising administering to a subject in need thereof a composition comprising sialyllactose as an active ingredient.

2. The method according to claim 1, wherein sialyllactose is α-NeuNAc-(2→3)-β-D-Gal-(1→4)-D-Glc or α-NeuNAc-(2→6)-β-D-Gal-(1→4)-D-Glc.

3. The method according to claim 2, wherein said sialyllactose is α-NeuNAc-(2→6)-β-D-Gal-(1β4)-D-Glc.

4. The method according to claim 1, wherein said sialyllactose inhibits proliferation of keloid fibroblasts or induces apoptosis of keloid fibroblasts.

5. The method according to claim 1, wherein the composition is a pharmaceutical composition.

6. The method according to claim 1, wherein the composition is a functional cosmetic composition.

* * * * *